(12) United States Patent
Rutter

(10) Patent No.: US 7,140,369 B2
(45) Date of Patent: Nov. 28, 2006

(54) TRACHEOTOMY ENDOTRACHEAL TUBE

(76) Inventor: Michael John Rutter, 1110 Brayton Ave., Cincinnati, OH (US) 45215

( * ) Notice: Subject to any disclaimer, the term of this patent is extended or adjusted under 35 U.S.C. 154(b) by 0 days.

(21) Appl. No.: 10/737,128

(22) Filed: Dec. 15, 2003

(65) Prior Publication Data

US 2004/0123869 A1 Jul. 1, 2004

Related U.S. Application Data

(60) Provisional application No. 60/433,736, filed on Dec. 16, 2002.

(51) Int. Cl.
*A61M 16/00* (2006.01)
*A62B 9/06* (2006.01)
(52) U.S. Cl. ............... 128/207.14; 128/207.15; 128/207.16; 128/207.29; 128/200.26; 128/912; 604/93.01
(58) Field of Classification Search ........... 128/200.26, 128/207.14, 207.15, 207.29, 912
See application file for complete search history.

(56) References Cited

U.S. PATENT DOCUMENTS

| | | | |
|---|---|---|---|
| 3,529,596 A | | 9/1970 | Garner |
| 3,599,642 A | | 8/1971 | Tindel |
| 3,964,488 A | | 6/1976 | Ring et al. |
| 4,340,046 A | | 7/1982 | Cox |
| 4,377,164 A | | 3/1983 | Sabbota |
| 4,471,776 A | * | 9/1984 | Cox ............ 128/207.15 |
| 4,593,690 A | * | 6/1986 | Sheridan et al. ...... 128/207.15 |
| 4,622,965 A | * | 11/1986 | Teeple ............ 128/207.14 |
| 4,987,895 A | | 1/1991 | Heimlich |
| 5,031,613 A | * | 7/1991 | Smith et al. ......... 128/207.14 |
| 5,058,577 A | | 10/1991 | Six |
| 5,245,992 A | * | 9/1993 | Nye ................. 128/200.26 |
| 5,333,608 A | | 8/1994 | Cummins |
| 5,339,809 A | * | 8/1994 | Beck et al. ......... 128/207.29 |
| 5,386,826 A | * | 2/1995 | Inglis et al. ........ 128/207.14 |
| 5,443,064 A | | 8/1995 | Theis et al. |
| 5,546,936 A | * | 8/1996 | Virag et al. ........ 128/207.14 |
| 5,582,167 A | * | 12/1996 | Joseph ............. 128/207.15 |
| 5,590,647 A | * | 1/1997 | Nye ................. 128/207.14 |
| 5,823,184 A | | 10/1998 | Gross |
| 5,840,065 A | * | 11/1998 | Goldhardt et al. ..... 604/170.03 |
| 6,705,320 B1 | * | 3/2004 | Anderson ........... 128/207.14 |

OTHER PUBLICATIONS

Nellcor, Critical Care Systems (5 pages), http://www.nellcor.com/products (Jul. 21, 2002).
Nellcor, Critical Care Systems "LGT-Laryngectomy Tubes" (2 pages), http//www.nellcor.co/products (Aug. 19, 2002).
Nellcor, Critical Care System Hi-Lo® Tracheal Tube (2 pages), http://www..nellcor.com/products (Aug. 15, 2002).
Nellcor, Critical Care System Shiley® TracheoSoft® XLT Tracheostomy Tubes (2 pages), http://www..nellcor.com/products (Aug. 15, 2002).

(Continued)

*Primary Examiner*—Henry Bennett
*Assistant Examiner*—Nihir Patel
(74) *Attorney, Agent, or Firm*—Ronald J. Richter; Donald E. Hasse; Hasse & Nesbitt LLC

(57) ABSTRACT

A flexible tracheotomy endotracheal tube comprises a short distal section of tubing, an intermediate section of tubing, a pre-formed obtuse-angle bend in the tube between the distal and intermediate sections, an elongated proximal section of tubing, a pre-formed abrupt bend in the tube between the intermediate and proximal sections, and an inflatable cuff integrated into the distal section of tubing.

16 Claims, 2 Drawing Sheets

OTHER PUBLICATIONS

Nellcor, Critical Care System Lo-Pro®/Lo-Contour® Tracheal Tube (4 pages), http://www..nellcor.com/products (Aug. 15, 2002).
Nellcor, Critical Care System Reinforced Tracheal Tube (2 pages), http://www..nellcor.com/products (Aug. 15, 2002).
Portex, Airway Management—ICU (1 page), http://www.portex.com/airway/products/department (Aug. 15, 2002).
Portex, Airway Management, Helping you sustain life (1 page), http://www.portex.com/airway/home (Aug. 15, 2002).
Nellcor, A Quick Reference Guide to Mallinckrodt Tracheal Tubes, Tracheal Tube Restraint (2 pages) and Nasal RAE Traceal Tube (1 page), http://www.nellcor.com/prod/Product (Oct. 20, 2003).

* cited by examiner

TRACHEOTOMY ENDOTRACHEAL TUBE

CROSS-REFERENCE TO RELATED APPLICATIONS

This application claims the benefit of U.S. Provisional Application No. 60/433,736, filed Dec. 16, 2002.

BACKGROUND OF THE INVENTION

The present invention relates to a tracheotomy endotracheal tube useful for delivering oxygen and anesthetic gases to a patient undergoing surgery. More particularly, the invention relates to a flexible tracheotomy endotracheal tube comprising a short distal section of tubing and an integrated cuff, a long proximal section of tubing, and an intermediate section of tubing connecting the distal and proximal sections through bends forming specified angles between the sections.

General anesthesia requires the delivery of oxygen and anesthetic gases to a patient's lungs during surgery. This may be done using a facemask, a laryngeal mask airway, or an endotracheal tube. Endotracheal tubes are available from several manufacturers, and in several styles. The tube may be cuffed or uncuffed. An inflated cuff allows a paralyzed patient to be ventilated with positive pressure without the air leaking back out the mouth. The tube may be straight or have a pre-formed bend to allow accurate placement of the tube without having to carefully measure its length below the vocal cords. A pre-formed bent tube is called an RAE tube. Both oral and nasal RAE tubes are available.

U.S. Pat. No. 3,964,488, Ring et al., issued Jun. 22, 1976, discloses a pre-formed, oral or nasal endotracheal tube made of flexible material having a memory such that the tube will return to its pre-formed shape following flexure. The endotracheal tube has distal and intermediate sections that merge with each other along the length of the tube, a proximal section that is substantially rectilinear, and an abrupt bend portion between the proximal and intermediate sections of the tube that forms an angle substantially no greater than ninety degrees.

U.S. Pat. No. 4,987,895, Heimlich, issued Jan. 29, 1991, discloses a cuffed tracheal tube that accommodates and follows the axial lengthening, shortening and translating movement of the trachea in actions such as breathing and swallowing. This minimizes relative movement between the trachea and the tube where the tube inner end engages and bears against the trachea.

While these and other endotracheal tubes are known in the art, administering anesthesia to patients via a tracheotomy, whether temporary or permanent, can still pose particular problems. Uncuffed tubes are prone to leak with positive pressure, especially if the diameter of the actual stoma is smaller than the diameter of the trachea. Straight endotracheal tubes get in the way if operating on the head and neck, and may kink if bent out of the way. Armored tubes do not kink but can be difficult to bend out of the way. Standard RAE tubes often are too long and need to be trimmed so they do not lie in a bronchus. A trimmed oral RAE tube is often used to deliver anesthesia to a patient with a tracheotomy, but it typically does not contain a cuff since any cuff would be cut off during trimming of the tube. Such a trimmed oral RAE tube may thus leak if the size of the stoma is smaller than the size of the trachea. Finally, the connection between the anesthetic tubing and the trimmed RAE tube generally lies on the patient's chest under surgical drapes, where it is difficult for the anesthesiologist to access.

Thus, there is a need for a tracheotomy endotracheal tube suitable for delivery of oxygen and anesthetic gases to a patient's lungs, which tube does not lie in a bronchus, does not leak during positive pressure ventilation, does not get in the way during surgery on the head and neck, and is readily accessible to the anesthesiologist.

BRIEF DESCRIPTION OF THE INVENTION

In one aspect, this invention provides a flexible tracheotomy endotracheal tube comprising:
(a) a short distal section of tubing;
(b) an intermediate section of tubing;
(c) a pre-formed obtuse-angle bend in the tube between the distal and intermediate sections;
(d) an elongated proximal section of tubing;
(e) a pre-formed abrupt bend in the tube between the intermediate and proximal sections; and
(f) an inflatable cuff integrated into the distal section of tubing.

In another aspect, the invention provides a flexible tracheotomy endotracheal tube comprising:
a) a short distal section of tubing;
b) an intermediate section of tubing;
c) a pre-formed obtuse-angle bend in the tube between the distal and intermediate sections;
d) an elongated proximal section of tubing;
e) a pre-formed abrupt bend in the tube between the intermediate and proximal sections; and
f) an inflatable cuff integrated into the distal section of tubing;

wherein the abrupt bend interconnects the proximal section and the intermediate section along the length of the tube at an angle of from about 80 to about 95 degrees, and the obtuse-angle bend interconnects the distal section and the intermediate section along the length of the tube at an angle of from about 105 to about 130 degrees; and wherein the distal section, the intermediate section, and the proximal section extend in the same general plane and are substantially rectilinear in formation.

BRIEF DESCRIPTION OF THE DRAWINGS

The aspects and advantages of the invention will be better understood from the following detailed description, with reference to the accompanying drawings, in which.

DETAILED DESCRIPTION OF THE INVENTION

The tracheotomy endotracheal tube of the present invention comprises a short distal section of tubing with an integrated inflatable cuff, a long proximal section of tubing, an intermediate section of tubing connecting the distal and proximal sections through bends forming specified angles between each connected pair of tube sections.

The short distal section of the tracheotomy endotracheal tube allows it to be placed in the trachea without risk of it lying in a bronchus, and without needing to trim the tube and its integrated cuff. The long proximal section of the tube allows an anesthesiologist to readily connect it to anesthetic tubing at a distance away from the patient's body. If the proximal section of the tube is too long, it can be easily trimmed to the desired length. The specified double angle in the tube accommodates the distance between the skin and the trachea, and the relative angles of the anterior chest wall and the trachea. The inflatable cuff on the distal section of tubing allows positive pressure ventilation without leakage even if a small tube is inserted through a small stoma into a large airway.

The tracheotomy endotracheal tube of the invention is primarily useful for patients requiring head and neck surgery with a temporary or permanent tracheotomy. However, it can also be used for any tracheotomy patient undergoing any form of surgery. It is useful for patients of all ages, and is especially useful for individuals undergoing airway surgery and for adults with cancer of the head and neck. It can also be used for managing ventilated tracheotomy patients on an intensive care unit.

Figure 1:
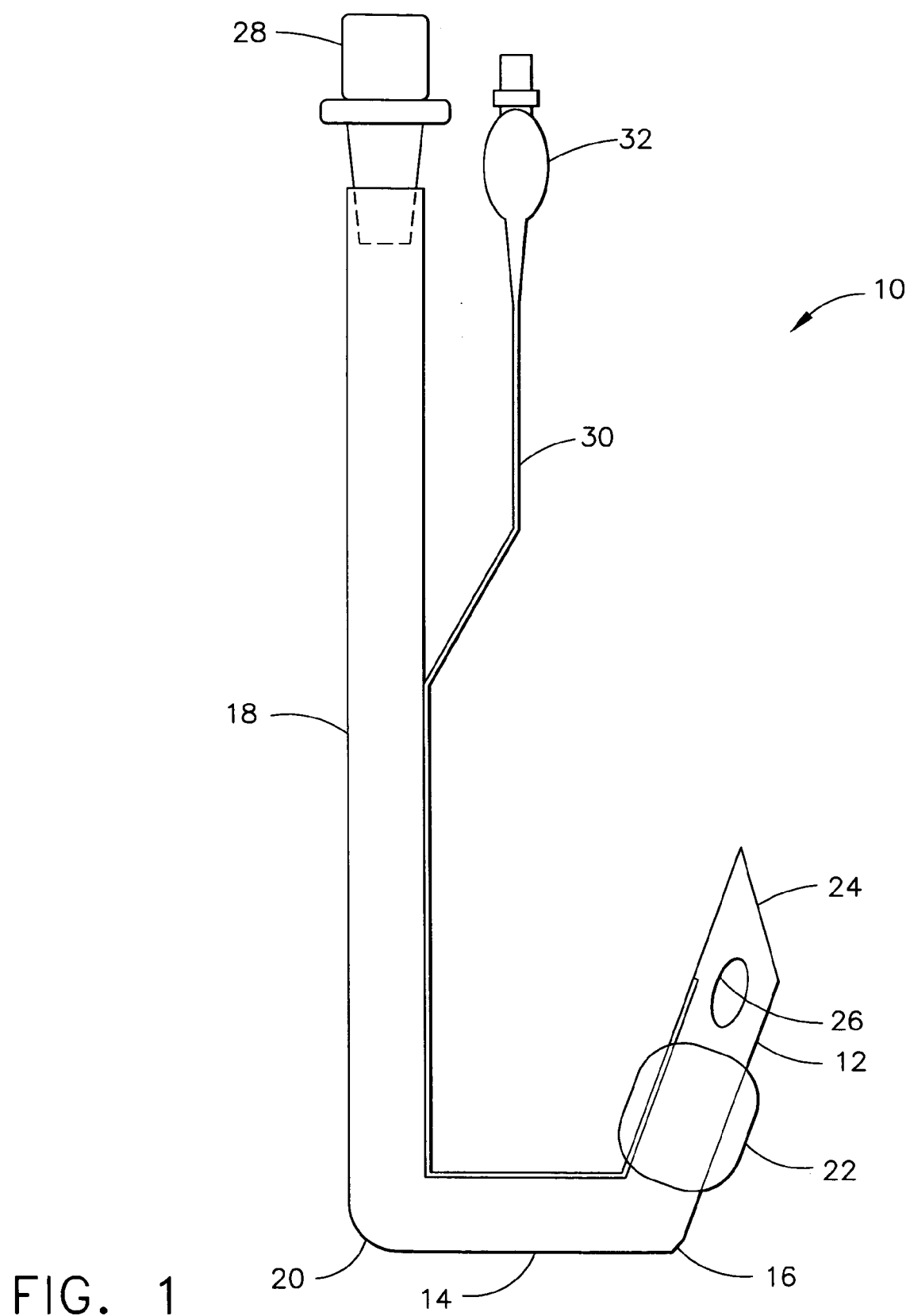
FIG. 1 is a plan view of a tracheotomy endotracheal tube of the invention.

For a better understanding of the invention, reference is now made to FIG. 1 of the drawings. FIG. 1 illustrates a tracheotomy endotracheal tube 10 of the invention having a short distal section 12 that is placed in the patient's trachea, an intermediate section 14, a pre-formed obtuse-angle bend 16 in the tube between the distal and intermediate sections, an elongated proximal section 18, a pre-formed abrupt bend 20 in the tube between the intermediate and proximal sections, and an inflatable cuff 22 integrated into, e.g., surrounding, the distal section of tubing.

As can be seen in FIG. 1, the distal section 12 and the adjoining intermediate section 14 smoothly merge into each other along the length of the tube through obtuse angle bend 16 such that they conform to the shape of a tracheotomy patient's stoma and trachea. The distal section 12 typically terminates in a beveled end, such as beveled end 24, that provides an outlet orifice (not shown) for delivering oxygen and anesthetic gases to the patient's lungs. The intermediate section 14 smoothly merges into abrupt bend 20, which in turn, smoothly merges into proximal section 18 of the endotracheal tube.

The proximal section 18 extends rectilinearly from abrupt bend 20, so as to extend downwardly along or outwardly from the chest of a patient when the endotracheal tube is installed, for conveniently administering anesthesia. Proximal section 18 could extend otherwise, however, for example, it could be slightly curved and askew from the rest of the tube. The intermediate section 14 and distal section 12 typically are both substantially rectilinear, and typically extend in the same general plane as the proximal section 18. The abrupt bend 20 usually forms about a 90-degree angle measured between an extension of the proximal section and an intersecting tangential extension of the intermediate section, so as to position the proximal section 18 exteriorly of the chest of the patient when installed. However, this angle may range from about 75 to about 100 degrees, more typically from about 80 to about 95 degrees.

Proximal section 18 terminates in a free end adapted for attachment to a machine with which the tube is to be used. A standard connector 28 can be used for connecting proximal section 18 to anesthetic tubing (not shown). Endotracheal tube 10 typically is of substantially uniform diameter externally and internally prior to attachment connector 28. Proximal section 18 is sufficiently long in any given size of tube 10 to position connector 28 away from the body cavity of the patient during use.

The obtuse angle bend 16 between distal section 12 and intermediate section 14 will depend upon the size of the device. As shown, the curvature of the former smoothly continues the curvature of the latter so that the entire curvature largely conforms to the patient's stoma and trachea. The obtuse angle typically ranges from about 100 to about 140 degrees, more typically from about 105 to about 130 degrees, e.g., from about 110 to about 120 degrees.

The length of the distal, intermediate, and proximal sections will vary depending on the size of the tracheotomy endotracheal tube, e.g., whether it is intended for use on an adult or a child. However, the distal section is typically about the same length as, or slightly longer than, the intermediate section. For example, the ratio of the length of the distal section to the length of the intermediate section may be from about 1.0 to about 2.0, typically from about 1.2 to about 1.8. The proximal section generally is at least twice as long as the distal section, and typically is about three times as long as the distal section. For example, the ratio of the length of the proximal section to the length of the distal section may be from about 2.0 to about 4.0, typically from about 2.5 to about 3.5.

An inflatable cuff 22 is located on and encircles distal section 12. When cuff 22 is inflated, it securely locates the distal section 12 in a patient's trachea and substantially prevents leakage of air back out the patient's mouth during positive pressure ventilation, as is understood in the art. An inflation tube 30 for inflating cuff 22 is also shown in FIG. 1. Inflation tube 30 has inflation openings (not shown) within cuff 22, and in the embodiment shown if FIG. 1, a closeable valve 32 on its end opposite cuff 22. Inflation tube 30 allows air under pressure to be passed through valve 32 into inflation tube 30 and expelled through the inflation openings to inflate cuff 22, sealing it against the inside surface of the trachea. Cuff 22 is typically constructed of a thin layer of plastic material that circumscribes distal section 12. When cuff 22 is in its deflated position, it has about the same diameter as distal section 12 so that it can easily be introduced into the trachea. When cuff 22 is inflated, it presents a balloonlike surface that is larger in diameter than the mean diameter of distal section 12, forming a seal between the trachea and the outer wall of distal section 12.

In one embodiment, a supplemental eye or port opening 26 adjacent to the beveled terminal end 24 of distal section 12 provides ventilation for the lungs as well as for the upper lobes should the tube be accidentally advanced onto the carina at the lower end of the trachea or into a main stem bronchus. A second eye or port opening (not shown) may be included in distal section 12, typically opposite port 26 and adjacent to terminal end 24, to help insure distribution of the oxygen and anesthetic gases to the lungs. Other than the outlet orifice and such port openings, the tube is typically imperforate.

Figure 2:
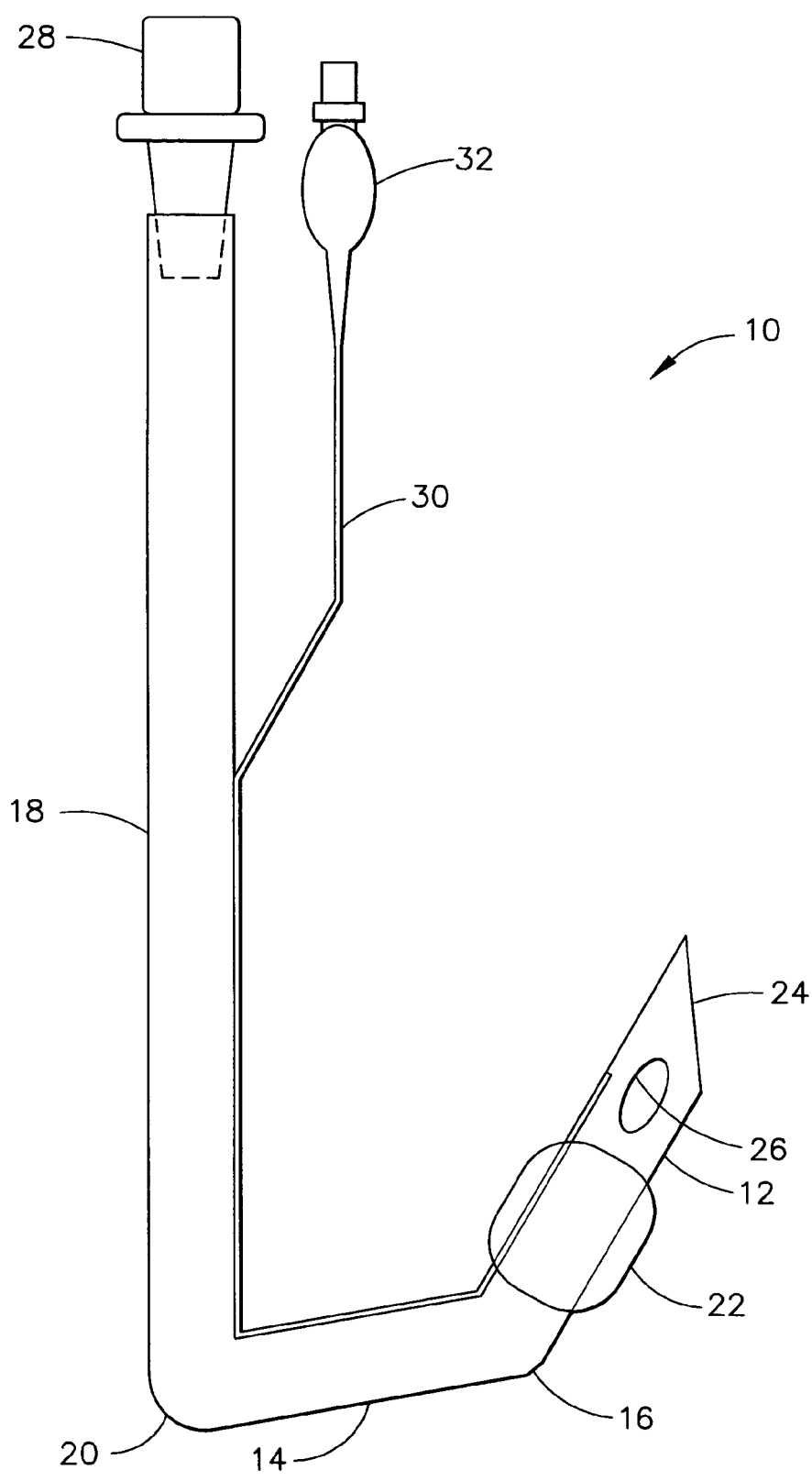
FIG. 2 is a plan view of an alternative tracheotomy endotracheal tube of the invention.

FIG. 2 shows an alternative tracheotomy endotracheal tube of the invention in which abrupt bend 20 forms about an 80-degree angle measured between an extension of proximal section 18 and intermediate section 14, and obtuse angle bend 16 forms about a 130-degree angle between an extension of intermediate section 14 and distal section 12.

The endotracheal tube herein is typically integrally preformed from a suitable flexible thermoplastic material, such as polyvinylchloride, polyethelyne, or the like, having a memory, i.e., having sufficient resiliency to return to position following flexure. Thus, although the tube has reasonable flexibility that enables it to conform to the environment rather than compelling the environment to conform to it, bend portions 16 and 20 essentially retain their configuration and are not subject to kinking during the administration of oxygen or an anesthetic.

The endotracheal tube of the invention is typically fabricated from suitable plastic materials of the type previously indicated having the required flexibility within the limits of the preformed formation. However, it is also possible to obtain the required "memory" for the preformed shape by incorporating one or more spring components that impart the required shape, memory, and non-kinking characteristics into a pliable non-preformed tube of suitable plastic or other material.

Although various embodiments of the invention have been described and exemplified, it will be understood that the scope of the invention is not limited to that description. Changes and modifications will occur to those of ordinary skill in the art and they can be made without departing from the spirit and scope of the invention. The invention is considered to include the methods of accomplishing the results described herein as well as structures designed to accomplish them.

As used herein, the term "comprising" means various components, capabilities and/or steps can be conjointly employed in the present invention. Accordingly, the term "comprising" encompasses the more restrictive terms "consisting essentially of" and "consisting of".

What is claimed is:

1. A flexible tracheotomy endotracheal tube comprising:
   a) a short distal section of tubing;
   b) an intermediate section of tubing;
   c) a pre-formed obtuse-angle bend in the tube between the distal and intermediate sections;
   d) an elongated proximal section of tubing;
   e) a pre-formed abrupt bend in the tube between the intermediate and proximal sections; and
   f) an inflatable cuff integrated into the distal section of tubing,
   wherein the obtuse-angle bend in the tube is from about 105 to about 130 degrees.

2. The endotracheal tube of claim 1 wherein the obtuse-angle bend in the tube is from about 110 to about 120 degrees.

3. The endotracheal tube of claim 2 wherein the abrupt bend interconnects the proximal section and the intermediate section along the length of the tube at approximately a right angle.

4. The endotracheal tube of claim 3 wherein the proximal section, the distal section and the intermediate section are substantially rectilinear in formation.

5. The endotracheal tube of claim 4 wherein all sections and bends of the flexible tube are made of a thermoplastic material preformed to the shape described.

6. The endotracheal tube of claim 5 wherein the distal section has a beveled terminal end with at least one part opening adjacent thereto, the tube being otherwise imperforate.

7. The endotracheal tube of claim 6 wherein the inflatable cuff securely locates the distal section in a patient's trachea and substantially prevents leakage of air back out the patient's mouth during positive pressure ventilation.

8. A flexible tracheotomy endotracheal tube comprising:
   a) a short distal section of tubing;
   b) an intermediate section of tubing;
   c) a pre-formed obtuse-angle bend in the tube between the distal and intermediate sections;
   d) an elongated proximal section of tubing;
   e) a pre-formed abrupt bend in the tube between the intermediate and proximal sections; and
   f) an inflatable cuff integrated into the distal section of tubing;
   wherein the abrupt bend interconnects the proximal section and the intermediate section along the length of the tube at an angle of from about 80 to about 95 degrees, and the obtuse-angle bend interconnects the distal section and the intermediate section along the length of the tube at an angle of from about 105 to about 130 degrees; and wherein the distal section, the intermediate section, and the proximal section extend in the same general plane and are substantially rectilinear in formation.

9. The endotracheal tube of claim 8 wherein all sections and bends of the flexible tube are made of a thermoplastic material preformed to the shape described.

10. The endotracheal tube of claim 9 wherein the abrupt bend interconnects the proximal section and the intermediate section along the length of the tube at approximately a right angle.

11. The endotracheal tube of claim 10 wherein the obtuse-angle bend in the tube is from about 110 to about 120 degrees.

12. The endotracheal tube of claim 11 wherein the distal section has a beveled terminal end with at least one port opening adjacent thereto, the tube being otherwise imperforate.

13. The endotracheal tube of claim 12 wherein the inflatable cuff securely locates the distal section in a patient's trachea and substantially prevents leakage of air back out the patient's mouth during positive pressure ventilation.

14. A flexible tracheotomy endotracheal tube comprising:
   a) a short distal section of tubing;
   b) an intermediate section of tubing;
   c) a pre-formed obtuse-angle bend in the tube between the distal and intermediate sections;
   d) an elongated proximal section of tubing;
   e) a pre-formed abrupt bend in the tube between the intermediate and proximal sections; and
   an inflatable cuff integrated into the distal section of tubing;
   wherein the abrupt bend interconnects the proximal section and the intermediate section along the length of the tube at an angle of from about 80 to about 95 degrees, and the obtuse-angle bend interconnects the distal section and the intermediate section along the length of the tube at an angle of from about 105 to about 130 degrees; wherein the distal section, the intermediate section, and the proximal section extend in the same general plane and are substantially rectilinear in formation; and wherein all sections and bends of the flexible tube are made of a thermoplastic material preformed to the shape described.

15. The endotracheal tube of claim 14 wherein the abrupt bend interconnects the proximal section and the intermediate section along the length of the tube at approximately a right angle.

16. The endotracheal tube of claim 15 wherein the obtuse-angle bend in the tube is from about 110 to about 120 degrees.

* * * * *